US00PP19560P2

(12) United States Plant Patent
Kanaya et al.

(10) Patent No.: US PP19,560 P2
(45) Date of Patent: Dec. 9, 2008

(54) ***PETUNIA* PLANT NAMED 'SUNSURFPASPIMI'**

(50) Latin Name: *Petunia×hybrida*
Varietal Denomination: Sunsurfpaspimi

(75) Inventors: Takeshi Kanaya, Shiga (JP); Yasuko Isobe, Shiga (JP); Kazunari Iwaki, Kanagawa (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/998,805

(22) Filed: Nov. 30, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Petunia* plant named 'Sunsurfpaspimi', characterized by its outwardly spreading and mounding plant habit; vigorous growth habit; freely branching and flowering plant habit; long flowering period; medium-sized pastel pink-colored flowers; and good garden performance.

1 Drawing Sheet

Botanical designation: *Petunia×hybrida.*
Cultivar denomination: 'SUNSURFPASPIMI'.

BACKGROUND OF THE INVENTION

The present invention relates to a new and distinct cultivar of *Petunia,* botanically known as *Petunia×hybrida* and hereinafter referred to by the name 'Sunsurfpaspimi'.

The new *Petunia* is a product of a planned breeding program conducted by the Inventors in Higashiomi, Shiga, Japan. The objective of the breeding program is to create new *Petunia* cultivars with attractive foliage and flower coloration.

The new *Petunia* originated from a cross-pollination made by the Inventors in September, 2003 in Higashiomi, Shiga, Japan of a proprietary selection of *Petunia×hybrida* identified as code number PS203-1, not patented, as the female, or seed, parent with a proprietary selection of *Petunia×hybrida* identified as code number PS312-1, not patented, as the male, or pollen, parent. The new *Petunia* was discovered and selected by the Inventors as a single flowering plant within the progeny of the stated cross-pollination in a controlled environment in Higashiomi, Shiga, Japan.

Asexual reproduction of the new *Petunia* by terminal cuttings in a controlled environment in Higashiomi, Shiga, Japan since September, 2005, has shown that the unique features of this new *Petunia* are stable and reproduced true to type in successive generations.

SUMMARY OF THE INVENTION

The cultivar Sunsurfpaspimi has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfpaspimi'. These characteristics in combination distinguish 'Sunsurfpaspimi' as a new and distinct cultivar of *Petunia:*

1. Outwardly spreading and mounding plant habit.
2. Vigorous growth habit.
3. Freely branching and flowering plant habit.
4. Long flowering period.
5. Medium-sized pastel pink-colored flowers.
6. Good garden performance.

Plants of the new *Petunia* can be compared to plants of the female parent selection. Plants of the new *Petunia* differ from plants of the female parent selection in the following characteristics:

1. Plants of the new *Petunia* are larger than plants of the female parent selection.
2. Plants of the new *Petunia* have larger flowers than plants of the female parent selection.

Plants of the new *Petunia* can be compared to plants of the male parent selection. Plants of the new *Petunia* differ from plants of the male parent selection in the following characteristics:

1. Plants of the new *Petunia* are more mounding than and not as trailing as plants of the male parent selection.
2. Plants of the new *Petunia* and the male parent selection differ in flower color as plants of the male parent selection have purple-colored flowers.

Plants of the new *Petunia* can also be compared to plants of the cultivar Sunsurfcopasaku, disclosed in U.S. Plant Pat. No. 18,122. In side-by-side comparisons conducted in Higashiomi, Shiga, Japan, plants of the new *Petunia* and the cultivar Sunsurfcopasaku differed in the following characteristics:

1. Plants of the new *Petunia* were larger than plants of the cultivar Sunsurfcopasaku.
2. Plants of the new *Petunia* had larger leaves than plants of the cultivar Sunsurfcopasaku.
3. Plants of the new *Petunia* had larger flowers than plants of the cultivar Sunsurfcopasaku.
4. Plants of the new *Petunia* and the cultivar Sunsurfcopasaku differed in petal shape.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a top perspective view of a typical flowering plant of 'Sunsurfpaspimi' grown in a container.

The photograph at the bottom of the sheet is a close-up view of typical flowers of 'Sunsurfpaspimi'.

DETAILED BOTANICAL DESCRIPTION

The aforementioned photographs and following observations, measurements and values describe plants grown in Higashiomi, Shiga, Japan, under commercial practice during the spring and summer in an outdoor nursery day temperatures averaging 23° C., and night temperatures averaging 13° C. Plants had been growing for about four months when the photographs and description were taken. In the following description, color references are made to The Royal Horticultural Society Colour Chart, 2001 Edition, except where general terms of ordinary dictionary significance are used.

BOTANICAL CLASSIFICATION: *Petunia×hybrida* cultivar Sunsurfpaspimi.

PARENTAGE:

*Female, or seed, parent.*—Proprietary selection of *Petunia×hybrids* identified as code number PS203-1, not patented.

*Male, or pollen, parent.*—Proprietary selection of *Petunia×hybrida* identified as code number PS312-1, not patented.

PROPAGATION:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous; light brown in color.

*Rooting habit.*—Freely branching.

Plant description:

*Plant and growth habit.*—Outwardly spreading and mounding plant habit. Freely branching with about 27 lateral branches developing per plant; pinching enhances lateral branch development. Vigorous growth habit.

*Plant height.*—About 19.4 cm.

*Plant diameter.*—About 48.2 cm.

LATERAL BRANCH DESCRIPTION:

*Length.*—About 17 cm.

*Diameter.*—About 1.5 mm.

*Internode lengthy.*—About 6 mm.

*Strength.*—Strong.

*Aspect.*—Initially upright to outward.

*Texture.*—Pubescent.

*Color.*—144A.

Foliage description:

*Arrangement.*—Before flowering, alternate, simple; after flowering, opposite, simple.

*Length.*—About 6 cm.

*Width.*—About 2.5 cm.

*Shape.*—Elliptic.

*Apex.*—Obtuse.

*Base.*—Obtuse.

*Margin.*—Entire.

*Texture, upper and lower surfaces.*—Pubescent.

*Venation pattern.*—Pinnate; reticulate.

*Color.*—Developing and fully expanded foliage, upper surface: 137B; venation, 144D. Developing and fully expanded foliage, lower surface: 146B; venation, 144D.

*Petiole.*—Length: About 8 mm. Diameter: About 1.3 mm. Texture, upper and lower surfaces: Sparsely pubescent. Color, upper and lower surfaces: 144D.

Flower description:

*Flower arrangement and habit.*—Single salverform flowers arising from leaf axils. Freely flowering habit with usually about 45 open flowers per plant. Flowers not persistent. Flowers face upright or outwardly. Flowers not fragrant.

*Natural flowering season.*—Plants of the new *Petunia* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant.

*Flower diameter.*—About 6.1 cm.

*Flower length (depths).*—About 4 cm.

*Throat diameter.*—About 1.2 cm.

*Tube diameter, base.*—About 2 mm.

*Tube length.*—About 3 cm.

*Flower bud.*—Shape: Cylindrical. Length: About 3.3 cm. Diameter: About 4.6 mm. Color: 75C.

*Corolla.*—Arrangement: Five petals fused at the base and opening into a flared trumpet. Petal length from throat: About 2.8 cm. Petal width: About 2.4 cm. Petal shape: Spatulate. Petal apex: Cuspidate. Petal margin: Entire; slightly undulate. Petal texture, upper and lower surfaces: Smooth, glabrous; velvety. Tube texture: Pubescent. Color: Petal, when opening, upper surface: Close to N74B. Petal, when opening, lower surface: Close to 76C. Petal, fully opened, upper surface: Close to N74D. Petal, fully opened, lower surface: Close to 76C. Throat: 162D. Tube: 75B.

*Calyx.*—Arrangement: One star-shaped calyx tube with five sepals fused at the base per flower. Sepal length: About 1.2 cm. Sepal width: About 1.1 mm. Sepal shape: Lanceolate. Sepal apex: Acute. Sepal margin: Entire. Sepal texture, upper and lower surfaces: Pubescent. Color, upper and lower surfaces: 144A.

*Pedunces.*—Length: About 1.3 cm. Diameter: About 0.8 mm. Strength: Strong. Texture: Smooth, glabrous. Color: 144A.

*Reproductive organs.*—Stamens: Quantity/arrangement: Five per flower. Anther shape: Ellipsoidal. Anther size: About 1.5 mm by 2 mm. Anther color: 155D. Pollen amount: Moderate. Pollen color: 155D. Pistils: Quantity: One per flower. Pistil length: About 1.5 cm. Style color: 145B. Stigma shape: Transversely ellipsoidal. Stigma color: N144D. Ovary color: 145A. Seed/fruit: Seed and fruit development have not been observed on plants of the new *Petunia.*

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia.*

What is claimed is:

1. A new and distinct Petunia plant named 'Sunsurfpaspimi' as illustrated and described.

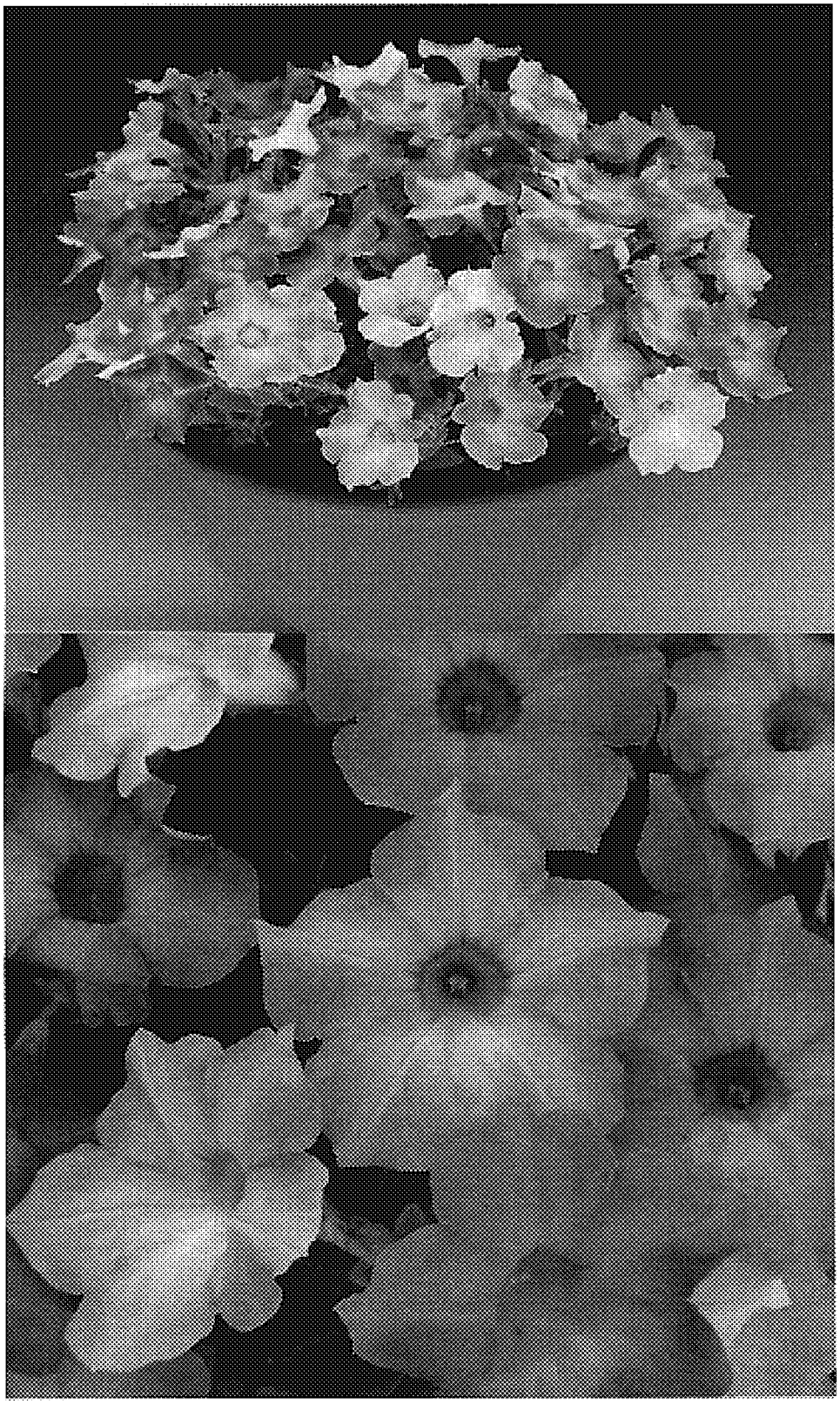

* * * * *